(12) United States Patent
Kloet et al.

(10) Patent No.: US 8,872,003 B2
(45) Date of Patent: Oct. 28, 2014

(54) RESISTANCE TO POST HARVEST DETERIORATION IN CUCUMBER

(75) Inventors: Johannes Willem Kloet, Moerkapelle (NL); Robert Hélène Ghislain Dirks, Oudenbosch (NL); Joyce Sylvia Velterop, Rijswijk (NL); Cornelis Maria Petrus Van Dun, Roosendaal (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 195 days.

(21) Appl. No.: 13/108,303

(22) Filed: May 16, 2011

(65) Prior Publication Data
US 2011/0277191 A1 Nov. 10, 2011

Related U.S. Application Data

(63) Continuation-in-part of application No. PCT/EP2009/065509, filed on Nov. 19, 2009.

(60) Provisional application No. 61/121,638, filed on Dec. 11, 2008.

(30) Foreign Application Priority Data

Nov. 19, 2008 (EP) .................... 08020156

(51) Int. Cl.
| | | |
|---|---|---|
| A01H 5/10 | (2006.01) | |
| A01H 5/00 | (2006.01) | |
| A01H 4/00 | (2006.01) | |
| A01H 5/08 | (2006.01) | |

(52) U.S. Cl.
CPC ....................... *A01H 5/08* (2013.01)
USPC ........... 800/307; 800/260; 800/266; 800/270; 800/276

(58) Field of Classification Search
None
See application file for complete search history.

(56) References Cited

U.S. PATENT DOCUMENTS

2006/0200875 A1 9/2006 Guo et al.

FOREIGN PATENT DOCUMENTS

| WO | WO 00/32761 | 6/2000 |
| WO | WO 03/018627 | 3/2003 |
| WO | WO 2007/042070 | 4/2007 |
| WO | WO 2007/077230 | 7/2007 |

OTHER PUBLICATIONS

McGrath, et al., Ethylene Signaling in *Arabidopsis*: Events From the Membrane to the Nucleus, Plant Physiol. Biochem. (1998) vol. 36, (1-2), p. 103-113.
Wehner, et al., Screening the Cucumber Germplasm Collection for Fruit Storage Ability, HortScience (2000) vol. 35, No. 4, p. 699-707.
Seiji Yamasaki, et al., The M Locus and Ethylene-Controlled Sex Determination in Andromonoecious Cucumber Plants, Plant Cell Physiol. (2001) vol. 42, No. 6, p. 608-619.
Seiji Yamasaki, et al., The Ethylene-Regulated Expression of CS-ETR2 and CS-ERS Genes in Cucumber Plants and Their Possible Involvement With Sex Expression in Flowers, Plant Cell Physiol. (2000) vol. 41, No. 5, p. 608-616.

*Primary Examiner* — Brent T Page
(74) *Attorney, Agent, or Firm* — Vedder Price P.C.; Thomas J. Kowalski; Deborah L. Lu

(57) ABSTRACT

The invention relates to a cucumber (*Cucumis sativus*) plant, which has the improved shelf life as found in plants and fruits grown from seeds of cucumber EX5001 representative seeds of which were deposited under NCIMB accession number 41670. The plant may be obtainable by crossing a cucumber plant with a plant grown from seeds of cucumber EX5001 representative seeds of which were deposited under NCIMB accession number 41670 and selecting in the F2 progeny of the cross that may be obtained after selfing the F1 for plants showing an improved shelf life.

9 Claims, 1 Drawing Sheet

RESISTANCE TO POST HARVEST DETERIORATION IN CUCUMBER

RELATED APPLICATIONS AND INCORPORATION BY REFERENCE

This application is a continuation-in-part application of international patent application Serial No. PCT/EP2009/065509 filed 19 Nov. 2009, which published as PCT Publication No. WO 2010/057960 on 27 May 2010, which claims benefit of European patent application Serial No. 08020156.9 filed 19 Nov. 2008 and U.S. provisional patent application Ser. No. 61/121,638 filed 11 Dec. 2008.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to cucumber (*Cucumis sativus* L.) plants showing a reduced susceptibility to post harvest deterioration of the cucumber fruits. The invention further relates to parts of the plants, in particular the fruits, to seeds and to other propagation material, and to progeny of the plants.

BACKGROUND OF THE INVENTION

Breeding of fruity vegetables like cucumber aims at the production of commercial varieties optimally adapted to a professional production environment in order to produce marketable products. Many characteristics need to be taken into account during selection which relate to both input and output traits. One of the most important traits in this respect relates to post harvest quality, in particular to the shelf life of fruits. The avoidance of post harvest deterioration of fruits is an important element that can significantly contribute to an economically more efficient arrangement of the whole production chain.

From the moment of harvest of the cucumber crop until the moment of consumption, the produce is exposed to different exogenous factors contributing to product deterioration. Such factors can be wounding during harvesting and processing, darkness and nutrient deficiency during storage and ethylene during processing, transport and storage. These factors strongly stimulate the post harvest disorders which can become apparent as yellowing or loss of firmness of the fruits. As a consequence of these effects the product becomes much less attractive and thereby unmarketable.

In order to counter the deterioration effects, many post harvest measurements can be taken which reduce these effects. For example, one can store the harvested cucumber fruits at relatively low temperatures of around 10° C. to retard senescence. In addition, logistic measurements may be implemented which reduce the transportation time required from the greenhouse or field to the consumer or which prevents the cucumber fruits to be stored in the vicinity of an ethylene source. Furthermore chemical treatments such as with 1-methylcyclopropene (1-MCP) or others may be applied to prevent the post harvest deterioration although food safety and consumer acceptance obviously become an issue.

Many of the post harvest measurements are successful to some extent but there is certainly room for improvement. Moreover, costs involved may be substantial, which is another reason to explore alternatives which reduce the need to apply post harvest treatments. Although knowledge of the physiology of post harvest deterioration is limited, senescence seems to play an important role in this respect.

Senescence is a naturally occurring, developmental process at the end of a life cycle of a plant or plant organ during which metabolism is reprogrammed in order to remobilize resources into reproductive structures like seeds. Yellowing of green leaves or immature green fruits is the most visible symptom of senescence. These are a consequence of chlorophyll breakdown during a relatively late stage of senescence.

Ethylene is an important plant hormone generally known to stimulate physiological processes related to senescence once a leaf or fruit is receptive. In cucumber this stimulation becomes apparent through the yellowing and reduced firmness of harvested fruits. Loss of fruit firmness relates to the enzymatic break down of cell wall constituents like pectine, cellulose and hemicellulose. As a consequence the tissue integrity of the fruits is gradually lost which leads to a strong increase of pathogen susceptibility which usually manifests by fungal growth at the fruit surface.

Although fruits of cucumber are known to produce only low amounts of ethylene, especially during the immature phase, the fruits are highly sensitive towards this plant hormone. Therefore, physiological disorders associated with ethylene sensitivity which reduce the post harvest quality of cucumber can be caused by endogenous ethylene synthesis but external sources of ethylene can also be very important in this respect. Exposure to such external sources can occur during harvesting, processing and storage of the produce.

For example, when cucumber fruits are transported or stored in the vicinity of ethylene producing fruits such as apples, pears, bananas or peaches severe deterioration may occur. Furthermore, when cucumber is processed and used as packaged fresh-cut product or in fresh-cut mixtures there may be limitations with respect to the ingredients which can be used due to ethylene release by one or more of the ingredients.

Although ethylene is the most important plant hormone known to stimulate senescence, other hormones like jasmonate may also contribute to this process.

However, in addition to playing a role in senescence, ethylene is also known to be involved in many other physiological processes. In cucumber ethylene plays an important role in the determination of sex expression of the flowers. In general, ethylene treatment of cucumber flower buds enhances femaleness. On the other hand when the sensitivity of female flower buds towards ethylene is reduced for example through the application of silver ions which bind the ethylene binding site of the ethylene receptor protein, the flowers will change their developmental program to enhance the development of male organs. A change in sex expression of the flowers is highly undesirable and must be avoided. It is generally thought that in cucumbers lowering the sensitivity to ethylene is not a suitable way of delaying post-harvest deterioration to increase shelf life.

Citation or identification of any document in this application is not an admission that such document is available as prior art to the present invention.

SUMMARY OF THE INVENTION

It is the object of the present invention to improve cucumber with respect to post harvest quality, which reduces or eliminates the need to take expensive, preventive measurements which are currently used to maintain the post harvest quality at a high level.

In the research leading to the present invention new cucumber plants were developed the fruits of which have an improved shelf life. It was found that these new plants show a reduced sensitivity to ethylene but surprisingly do not show a change in sex expression.

The present invention thus provides a cucumber (Cucumis sativus) plant, which has the improved shelf life as found in plants and fruits grown from seeds of cucumber EX5001 representative seeds of which were deposited under NCIMB accession number 41670. Cucumber EX5001 is a mutant plant.

The present invention also provides a cucumber (Cucumis sativus) plant, which has the reduced sensitivity to ethylene as found in plants grown from seeds of cucumber EX5001 representative seeds of which were deposited under NCIMB accession number 41670.

In one embodiment, the invention relates to a cucumber plant, which has an improved shelf life as compared to a control plant that has a normal shelf life, which plant is obtainable by crossing a cucumber plant with a plant grown from seeds of cucumber EX5001 representative seeds of which were deposited under NCIMB accession number 41670 and selecting in the progeny of the cross for plants showing an improved shelf life. The trait is recessive and selection is thus suitably made in the second generation of the cross (F2).

In one embodiment, the invention relates to a cucumber plant, which shows reduced sensitivity to ethylene as compared to a control plant that has a normal sensitivity to ethylene, which plant is obtainable by crossing a cucumber plant with a plant grown from seeds of cucumber EX5001 representative seeds of which were deposited under NCIMB accession number 41670 and selecting in the progeny of the cross for plants showing a reduced sensitivity to ethylene. The trait is recessive and selection is thus suitably made in the second generation of the cross (F2).

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposit with NCIMB Ltd., Ferguson Building, Craibstone Estate, Bucksburn, Aberdeen, AB21 9YA Scotland, UK, under deposit accession number NCIMB 41670 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
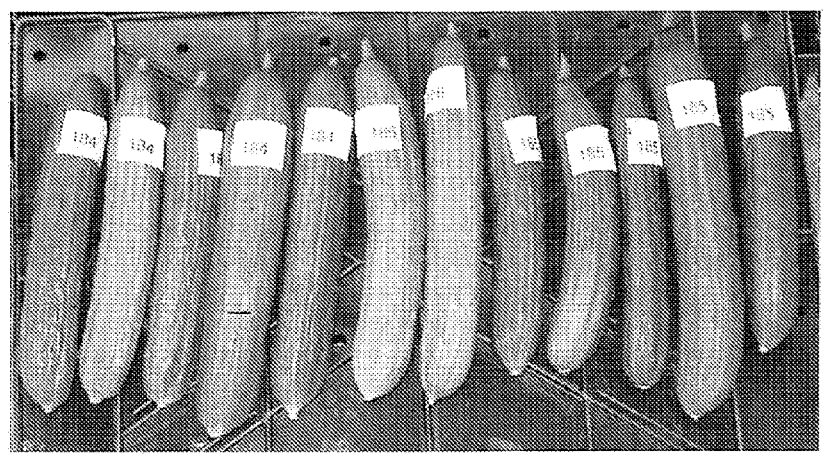
FIG. 1: Appearance of harvested cucumber fruits after 8 days exposure to 5 ppm ethylene. The fruits labeled 186 are derived from the negative control line. The fruits labeled 184 and 185 are derived from ethylene insensitive events 15 and 20 (EX5001), respectively. The skin of the fruits of the ethylene insensitive events are darker green as compared to the negative control.

The improved shelf life of the fruits of plants of the invention is directly linked to reduced sensitivity of the plant to ethylene. The reduced susceptibility or sensitivity to ethylene according to the invention does not have a detrimental effect on the sex expression of the flowers and is thus a special form of ethylene insensitivity. This reduced sensitivity to ethylene without affecting the sex expression and leading to a better post harvest shelf life is found to be a recessive trait that can phenotypically be detected in the second generation of a cross between any cucumber plant and a plant grown from a plant that shows the trait as found in the deposited seed, in particular a plant grown from the deposited seed, or any progeny plant thereof that has retained the trait.

The presence of the trait of the invention in a cucumber plant can be phenotypically detected in various ways, in particular in a seedling test as described below or by assessing the shelf life of the cucumber fruits with respect to colour and/or firmness and/or fungal growth on the surface. Also, combinations of these tests can be used.

The reduced sensitivity to ethylene can be determined on the basis of the relative growth of etiolated seedlings grown from the seed under an ethylene containing atmosphere as compared to air (the so-called "seedling test"). If the ratio between the average hypocotyl length of etiolated seedlings grown in darkness in air containing ethylene and the average hypocotyl length of etiolated seedlings grown in darkness in air is higher than 0.12 the seedling and therefore the plant that can be grown therefrom is insensitive to ethylene according to the invention. This ratio is also called the "score in the seedling test".

In one embodiment, an ethylene insensitive plant of the invention has a score in the seedling test of at least 0.15.

In one embodiment, an ethylene insensitive plant of the invention has a score in the seedling test of at least 0.20.

In one embodiment, an ethylene insensitive plant of the invention has a score in the seedling test of at least 0.25.

In one embodiment, an ethylene insensitive plant of the invention has a score in the seedling test of at least 0.30.

In one embodiment, an ethylene insensitive plant of the invention has a score in the seedling test of at least 0.35.

In one embodiment, an ethylene insensitive plant of the invention has a score in the seedling test of at least 0.40.

The result of the seedling test can also be expressed as percentage difference in hypocotyl length. The values above are then multiplied by 100.

Another phenotypic parameter that is relevant to the post harvest shelf life is the appearance of harvested cucumber fruits after storage in the presence of ethylene. Mutant plants that have the improved shelf life and reduced sensitivity to ethylene of the invention remain firm and free of fungal growth after at least 8 days of exposure to ethylene.

In one embodiment, a plant of the invention with improved shelf life remains firm and free of fungal growth after at least 10 days of exposure to ethylene.

In one embodiment, a plant of the invention with improved shelf life remains firm and free of fungal growth after at least 12 days of exposure to ethylene.

A further parameter related to an improved shelf life is the firmness of the fruits as tested with a penetrometer. The average force expressed as $kg/cm^2$ required to penetrate the fruit flesh is significantly higher for fruits of plants of the invention than for control fruits that are sensitive to ethylene. The difference may vary from 0.5 to 0.9 $kg/cm^2$ or more.

In one embodiment of the invention a cucumber plant is provided the fruits of which show an improved shelf life and thus when crossed with a tester plant grown from seed of *Cucumis sativus* EX5001 as deposited with the NCIMB under accession number NCIMB 41670 which comprises the improved shelf life trait of the invention, or a progeny plant thereof that comprises the improved shelf life trait comprised in *Cucumis sativus* EX5001 as deposited with the NCIMB under accession number NCIMB 41670 or a plant derived from Cucumis sativus EX5001 as deposited with the NCIMB under accession number NCIMB 41670 and comprising the improved shelf life trait, plants of the first generation progeny of said cross show a 1:0 segregation for the improved shelf life.

Plants of the second and further generations, if obtained by selfing also show a 1:0 segregation for the improved shelf life since the trait is recessive and only phenotypically expressed when present in homozygous state.

In one embodiment of the invention a cucumber plant is provided which shows a reduced sensitivity to ethylene and thus when crossed with a tester plant grown from seed of *Cucumis sativus* EX5001 as deposited with the NCIMB under accession number NCIMB 41670 which comprises the ethylene insensitivity trait of the invention, or a progeny plant thereof that comprises the ethylene insensitivity trait comprised in *Cucumis sativus* EX5001 as deposited with the NCIMB under accession number NCIMB 41670 or a plant derived from *Cucumis sativus* EX5001 as deposited with the NCIMB under accession number NCIMB 41670 and comprising the ethylene insensitivity trait, plants of the first generation progeny of said cross show a 1:0 segregation for the reduces susceptibility to ethylene.

Plants of the second and further generations, if obtained by selfing also show a 1:0 segregation for the reduced ethylene susceptibility.

The improved shelf life of cucumbers of the invention has a genetic basis in the cucumber's genome. It is not exactly known which locus is responsible for the improved shelf life or the reduced ethylene sensitivity and what the improved shelf life or reduced ethylene sensitivity alleles are. With the above described cross with a tester plant a plant of the invention can be identified as having the same locus that is responsible for the observed phenotype.

It is possible to pyramide multiple alleles of reduced susceptibility towards ethylene.

Progeny of the plants as claimed are also part of this invention. "Progeny" as used herein is intended to encompass all plants having the same or a similar improved shelf life and the corresponding reduced susceptibility towards ethylene and physiological disorders, in particular fruit yellowing and loss of fruit firmness, as the original plants described herein and being derived therefrom in any way, such as by crossing, haploid culture, protoplast fusion or other techniques. Such progeny is not only the first but also all further generations as long as the reduced susceptibility is retained.

The mutant plants of the invention were obtained by a chemical random mutagenesis procedure combined with an efficient phenotypic selection procedure based on a response of etiolated seedlings to ethylene. Such seedling based selection system is by far more efficient in terms of numbers of plants which can be assessed per man hour as compared to the use of mature cucumber fruits. Furthermore, the time to produce plant material for screening is obviously much more reduced in the case of seedlings as compared to immature fruits. A further advantage of this approach is the use of the selection conditions at the seedling stage as predictive phenotypic marker for the post harvest trait in consecutive generations once a successful event has been identified.

In order to determine the response of the etiolated cucumber seedlings towards ethylene, use was made of especially designed plastic containers in which cucumber seedlings were grown on filter papers under an atmosphere in which ethylene levels can be varied. It was indeed found that the cucumber seedlings responded to the presence of ethylene by a reduced elongation of the hypocotyl which in principle would allow to select for ethylene insensitive mutants in case such mutants reside in the available population and in case the insensitivity is expressed phenotypically at the seedling level under the experimental conditions which were applied.

By growing large numbers of etiolated cucumber seedlings from a population containing randomly induced mutations under an ethylene containing atmosphere, it was thus surprisingly found that seedlings showing reduced ethylene sensitivity as compared to the ethylene sensitivity of the starting population can be obtained. Out of a population of approximately 40.000 M2 seedlings, those seedlings were selected which showed hypocotyl elongation which was significantly larger as compared to the average hypocotyl elongation of the whole population. The 46 seedlings identified in this manner were qualified as being putatively less sensitive to ethylene as compared to the control.

The M2 plants thus selected on the basis of a reduced response to ethylene were used to grow M3 seeds. Subsequently, the inbred lines descending from the ethylene insensitive events which successfully produced M3 seeds were re-evaluated for their response to ethylene. The level of insensitivity of each inbred line was scored on the basis of the relative growth of the seedling under an ethylene containing atmosphere versus air. Based on this criterion 27/31 events were now classified as being confirmed insensitive. Apparently and unexpectedly, genetic variation existed which leads to differences in the average etiolation response depending on the level of ethylene insensitivity. This insensitivity led to a change in sex-expression of the floral organs but only in those events which showed the largest insensitivity response as judged by the length of the etiolated hypocotyls. It was surprisingly found that within the collection of ethylene insensitive mutants a number of events could be identified which were not affected in sex expression of their floral organs. These events were used to develop plants of the invention.

The inbred lines which showed a confirmed ethylene insensitivity in the ethylene test and which were not changed in their sex expression were resown and grown in a greenhouse under regular cucumber production conditions to produce immature (but harvest mature) fruits that were harvested and assessed for yellowing under an atmosphere containing ethylene. As negative controls ethylene sensitive plants were grown which originate from the population and which were used to select the ethylene insensitive events.

Surprisingly, the seeds of all ethylene insensitive mutants germinated normally i.e. comparable to the seeds of a near-isogenic ethylene sensitive control plant when planted in potting soil. After cultivation, immature fruits were harvested and exposed to ethylene. One week of post-harvest incubation of fruits at 20° C. under a 5 ppm ethylene containing atmosphere resulted in a strong induction of yellowing of the fruits of the ethylene sensitive control plants. However, the ethylene insensitive events which were assessed for fruit quality and which were not affected in sex expression showed a significant reduction of yellowing. In addition, the fruits of the ethylene insensitive mutants were significantly more firm after exposure to ethylene as compared to fruits of ethylene sensitive control plants.

These results surprisingly demonstrate that ethylene insensitivity which was selected for at the seedling level can reduce physiological disorders at the mature plant level, even at the post harvest stage. It is furthermore surprisingly demonstrated that relatively low levels of ethylene insensitivity do not lead to a change in sex expression in cucumber but are apparently sufficient to provide a significant improvement of the post harvest quality of the fruits.

The invention further relates to seed of the cucumber plant of the invention and to parts of the plant that are suitable for sexual reproduction, i.e. propagation material. Such parts are for example selected from the group consisting of microspores, pollen, ovaries, ovules, embryo sacs and egg cells. In addition, the invention relates to parts of the plant that are suitable for vegetative reproduction, in particular cuttings, roots, stems, cells, protoplasts, etc.

According to a further aspect thereof, the invention provides a tissue culture of the cucumber plant of the invention. The tissue culture comprises regenerable cells. Such tissue culture can be derived from leaves, pollen, embryos, cotyledon, hypocotyls, meristematic cells, roots, root tips, anthers, flowers, seeds and stems.

According to another aspect of the invention cucumber plants are provided that have the same or similar improved shelf life and/or ethylene insensitivity as cucumber plants of the invention, of which representative seed was deposited under NCIMB Accession number NCIMB 41670, which plants are grown from seeds of the plant of the invention or regenerated from parts thereof, or from a tissue culture.

The invention also relates to progeny of the cucumber plant of the invention. Such progeny can be produced by sexual or vegetative reproduction of a plant of the invention or a progeny plant thereof. The regenerated progeny plant has the same or similar improved shelf life and/or ethylene insensitivity as the plant, of which representative seed was deposited under NCIMB Accession number NCIMB 41670. This means that such progeny has the same characteristics as claimed for the cucumber plant of the invention. In addition to this, the plant may be modified in one or more other characteristics. Such additional modifications are for example effected by mutagenesis or by transformation with a transgene.

The invention furthermore relates to hybrid seed and to a method of producing hybrid seed comprising crossing a first parent plant with a second parent plant and harvesting the resultant hybrid seed, wherein said first parent plant and said second parent plant are a plant as claimed.

It is clear that the parent that provides the trait of the invention is not necessarily a plant grown directly from the deposited seeds. The parent can also be a progeny plant from the seed or a progeny plant from seeds that are identified to have the trait of the invention by other means.

In this application the terms "reduced susceptibility to ethylene", "insensitivity to ethylene", "less sensitive to ethylene" and "lower sensitivity to ethylene" are used interchangeably. The terms mean that the effect of ethylene on the post harvest quality of the cucumber fruits formed by plants of the invention is reduced in that the plants have a longer shelf life as illustrated by a longer period during which the cucumber fruits retain their green colour, remain more firm and do not show fungal growth at their surface as compared to a control that does not have the trait of the invention. In addition, the plants of the invention do not show an affected sex expression.

"Improved shelf life trait" as used herein is intended to encompass a phenotypically detectable improvement in the shelf life of the fruits as defined herein with respect to colour and firmness. This trait has a genetic basis in the plant and is present in the genome of the plant but is detected in the fruits.

"Ethylene insensitivity trait" as used herein is intended to encompass a score in the seedling test as defined herein of higher than 0.12 (12%), in particular 0.19 (19%) or higher.

The two traits have in fact the same genetic basis but are named herein after the method by which they are assessed.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Genetic Modification of Cucumber by Ethyl Methane Sulfonate (ems)

Seeds of the cucumber breeding line BF11 were treated with ems by submergence of approximately 5000 seeds into an aerated solution of 0.07% (w/v) ems during 24 hours at room temperature.

The treated seeds were germinated and the resulting plants were grown in a greenhouse to produce seeds.

After maturation, M2 seeds were harvested and bulked in one pool. The resulting pool of M2 seeds was used as starting material to identify the individual M2 plants containing reduced sensitivity to ethylene.

The efficacy of the genetic modification procedure was assessed by determining the occurrence of bleached plants, which is indicative for chlorophyll loss due to modifications in genes directly or indirectly involved in the formation or accumulation of chlorophyll.

Example 2

Identification of Cucumber Plants which have Obtained Reduced Sensitivity to Ethylene M2 cucumber seeds were germinated on paper in a small plastic container with an ethylene concentration of 10-20 vpm (volume parts per million) at 21° C. in the dark. 1 Vpm contains 0.41 μmol/litre or 1.14 μg/litre. Ethylene-insensitive mutants were compared to ethylene-sensitive controls, and selected on the basis of an elongated hypocotyl when grown in darkness.

The ethylene-insensitive mutants which were obtained were grown in a greenhouse in order to produce M3-lines by self-fertilisation. In total 31 M3-lines were analysed with the seedling-test to confirm the ethylene insensitivity. When on average the emerged seedlings had produced a longer hypocotyl the event was qualified as being ethylene insensitive. In total 27 out of 31 events were given this qualification. When a line was segregating for ethylene-insensitivity, plants were selected and after an additional cycle of inbreeding a final seedling-test was performed to select homozygous ethylene-insensitive lines.

Ethylene-insensitive mutants were identified by their longer hypocotyls in comparison with sensitive control line, BF11. Results are presented in Table 1.

TABLE 1

The average hypocotyl length of etiolated seedlings of M3 lines derived from putative ethylene insensitive events (ID column) when grown in darkness in air (air column) or in air containing ethylene (ethylene column).

| ID | air | ethylene | % ethylene/air | S/R |
|---|---|---|---|---|
| (−) control | 10 | 1.0 | 10 | S |
| 2 | 10 | 4.2 | 41 | R |
| 3 | 12 | 3.8 | 32 | R |
| 4 | 12 | 1.0 | 8 | S |
| 5 | 13 | 3.3 | 27 | R |
| 6 | 13 | 4.1 | 32 | R |
| 8 | 10 | 3.2 | 32 | R |
| 9 | 11 | 3.3 | 31 | R |
| 10 | 13 | 1.8 | 15 | R |
| 11 | 12 | 2.0 | 17 | R |
| 12 | 10 | 1.0 | 10 | S |
| 13 | 11 | 2.8 | 26 | R |
| 14 | 10 | 1.7 | 17 | R |
| 15 | 10 | 3.4 | 33 | R |
| 16 | 10 | 2.1 | 20 | R |
| 17 | 10 | 1.5 | 15 | R |
| 18 | 10 | 2.8 | 29 | R |
| 19 | 10 | 2.6 | 27 | R |
| 20 | 17 | 3.3 | 19 | R |
| 21 | 9 | 2.4 | 28 | R |
| 22 | 9 | 2.1 | 25 | R |
| 25 | 10 | 1.9 | 18 | R |
| 30 | 9 | 1.0 | 12 | S |
| 31 | 10 | 2.9 | 29 | R |
| 32 | 10 | 2.8 | 28 | R |
| 33 | 9 | 3.0 | 35 | R |
| 34 | 8 | 1.9 | 23 | R |
| 40 | 10 | 1.0 | 10 | S |
| 42 | 10 | 1.9 | 19 | R |

TABLE 1-continued

The average hypocotyl length of etiolated seedlings of M3 lines derived from putative ethylene insensitive events (ID column) when grown in darkness in air (air column) or in air containing ethylene (ethylene column).

| ID | air | ethylene | % ethylene/air | S/R |
|---|---|---|---|---|
| 44 | 11 | 2.6 | 24 | R |
| 45 | 9 | 3.8 | 43 | R |
| 46 | 9 | 2.3 | 25 | R |

The ratio of the average hypocotyl length is shown as well (% ethylene/air column). The S/R column shows the scores for each of the events as being sensitive to ethylene (S) or insensitive to ethylene (R). The (−) control is the cucumber starting line which is used to produce the M2 population used in the ethylene insensitivity screens described in this invention.

Of these results event 20 was selected for the deposit. Seeds of Cucumis sativus EX5001 (which are seeds of the M3 line ID 20 in Table 1) were deposited on 2 Nov. 2009 with NCIMB Ltd., Ferguson Building, Craibstone Estate, Bucksburn, Aberdeen, AB21 9YA Scotland, UK and given the accession number NCIMB 41670.

Example 3

Identification of Ethylene Insensitive Cucumber Plants which have Obtained Reduced Post Harvest Deterioration with Respect to Fruit Yellowing and Fruit Firmness A number of confirmed ethylene insensitive events (at the level of seedling etiolation response in air containing ethylene) which were not changed with respect to sex-expression were evaluated for fruit shelf life when exposed to ethylene. Per event 5-8 fruits were collected and incubated at 21° C. in darkness under an atmosphere containing 5 ppm ethylene.

After 8 days, the negative control line BF11 (which represents the genetic background of each of the mutants) turned from green to almost completely yellow as expected. The ethylene insensitive mutants also changed color but the fruits were less yellow as compared to the control fruits (FIG. 1).

A similar result was obtained when the fruits were compared during a shelf life experiment in air. The shelf life therefore seems to be enhanced under different storage conditions.

At this stage, fruit firmness was determined for a number of fruits of each event by cutting the fruit lengthwise in half and subsequently measuring the resistance of the fruit flesh at different positions of the fruit by using a penetrometer. The average force expressed as $Kg/cm^2$ required to penetrate the fruit flesh was 4.4 for the negative control fruits and 5.3 for the ethylene insensitive fruits. The results clearly show that the ethylene insensitive fruits had retained a higher levels of firmness as compared to the negative control fruits.

Figure 2:
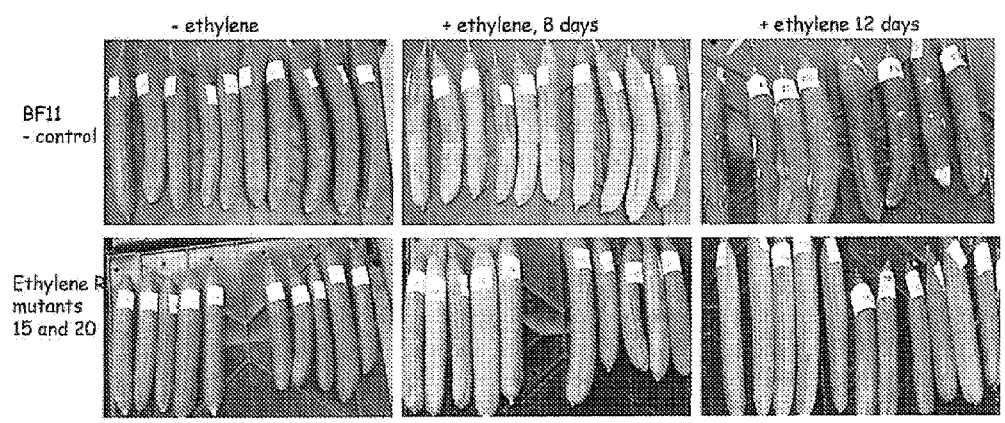
FIG. 2: Appearance of harvested cucumber fruits after 0 (left column), 8 (middle column) and 12 (right column) days exposure to 5 ppm ethylene. The negative control fruits are depicted in the upper row whereas the fruit from the ethylene insensitive mutants are shown in the lower row. On the left fruits from event 15 and on the right fruit from event 20 (EX5001) are shown.

Upon manual recording this effect could clearly be ascertained. The negative control fruits were soft and could easily be bended without breaking whereas the ethylene insensitive fruits were still firm. Prolonged exposure up to 12 days to ethylene resulted in further deterioration of the control fruits and as a consequence fungal growth at the surface became visible. The ethylene insensitive fruits, despite losing some of their color, remained firm and free of fungal growth (FIG. 2). Therefore, it is concluded that the ethylene insensitivity in cucumber according to the invention is a trait that improves the post harvest quality of cucumbers.

Example 4

Transfer of the Improved Post Harvest Quality Trait to Other Cucumbers

The improved post harvest quality trait in Cucumis sativus plants of EX5001, deposited under NCIMB accession number 41670, were crossed into a Cucumis sativus plant lacking such trait.

First, plants of EX5001 were crossed with an ethylene sensitive plant: cultivar Roxanna of Rijk Zwaan.

The resulting F1 plants were selfed in order to produce an F2 with plants comprising the trait. From the selfed F2 population those plants which were insensitive to ethylene were selected by conducting a seedling test as described in example 2.

This way it was possible to transfer the trait of the invention to ethylene sensitive cucumbers thus conferring the improved shelf life to their fruits.

The invention is further described by the following numbered paragraphs:

1. Cucumber (Cucumis sativus) plant, which has the improved shelf life as found in plants and fruits grown from seeds of cucumber EX5001 representative seeds of which were deposited under NCIMB accession number 41670.
2. Cucumber plant of paragraph 1, the fruits of which have an improved shelf life as compared to the fruits of a control plant that have a normal shelf life, and which plant is obtainable by crossing a cucumber plant with a plant grown from seeds of cucumber EX5001 representative seeds of which were deposited with the NCIMB under NCIMB accession number 41670 and selecting in the F2 progeny of the cross that is obtained after selfing the F1 for plants showing an improved shelf life.
3. Cucumber plant of paragraph 1 or 2, wherein the harvested cucumber fruits after storage in the presence of ethylene remain firm and free of fungal growth after at least 8 days of exposure to ethylene.
4. Cucumber plant of paragraph 1, 2 or 3, the fruits of which show reduced sensitivity to ethylene as compared to the fruits of a control plant that have a normal sensitivity to ethylene.
5. Cucumber plant of paragraph 4, wherein the plant is insensitive to ethylene if the ratio between the average hypocotyl length of the plant in etiolated seedling stage grown in darkness in air containing ethylene and the average hypocotyl length of the plant in etiolated seedling stage grown in darkness in air is higher than 0.12.
6. Cucumber plant of paragraph 5, wherein the ratio is 0.19 or higher.
7. Seed of a cucumber plant of any one of paragraphs 1 to 6.
8. Progeny of a cucumber plant or cucumber seeds of any one of paragraphs 1 to 7.
9. Propagation material of a plant of any one of paragraphs 1 to 8.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A cucumber (*Cucumis sativus*) plant having genetic information for expressing ethylene insensitivity and resulting in ethylene insensitivity, wherein the genetic information is as contained in a plant, representative seed of which were deposited under NCIMB accession number 41670, and wherein ethylene insensitivity results in a cucumber fruit having a shelf life greater than a cucumber fruit from a plant not having the genetic information.
2. The cucumber plant as claimed in claim 1 obtainable by crossing a cucumber plant with a plant grown from seeds of cucumber EX5001, representative seeds of which were deposited with the NCIMB under NCIMB accession number 41670 and selecting plants for ethylene insensitivity in the F2 progeny of the cross that is obtained after selfing the F1.
3. The cucumber plant as claimed in claim 1, wherein the harvested cucumber fruits after storage in the presence of ethylene remain firm and free of fungal growth after at least 8 days of exposure to ethylene.
4. The cucumber plant as claimed in claim 1, the fruits of which show reduced sensitivity to ethylene as compared to the fruit of a control plant that have a normal sensitivity to ethylene.
5. The cucumber plant as claimed in claim 4, wherein the plant is insensitive to ethylene if the ratio between the average hypocotyl length of the plant in etiolated seedling stage grown in darkness in air containing ethylene and the average hypocotyl length of the plant in etiolated seedling stage grown in darkness in air is higher than 0.12.
6. The cucumber plant as claimed in claim 5, wherein the ratio is 0.19 or higher.
7. Seed of a cucumber plant as claimed in claim 1.
8. Progeny of a cucumber plant or cucumber seeds as claimed in claim 1.
9. Propagation material of a plant as claimed in claim 1.

\* \* \* \* \*